(12) United States Patent
Orr et al.

(10) Patent No.: US 11,701,210 B2
(45) Date of Patent: Jul. 18, 2023

(54) EQUINE THERMAL THERAPY OVERLEG DEVICE

(71) Applicants: Susan B. Orr, Jacksonville Beach, FL (US); Joan C. Gariboldi, Lexington, KY (US)

(72) Inventors: Susan B. Orr, Jacksonville Beach, FL (US); Joan C. Gariboldi, Lexington, KY (US)

( * ) Notice: Subject to any disclaimer, the term of this patent is extended or adjusted under 35 U.S.C. 154(b) by 692 days.

(21) Appl. No.: 16/786,192

(22) Filed: Feb. 10, 2020

(65) Prior Publication Data

US 2020/0170770 A1 Jun. 4, 2020

Related U.S. Application Data

(63) Continuation-in-part of application No. 15/626,081, filed on Jun. 17, 2017, now abandoned.

(60) Provisional application No. 62/351,955, filed on Jun. 18, 2016.

(51) Int. Cl.

| A61D 9/00 | (2006.01) |
|---|---|
| A61F 7/10 | (2006.01) |
| A61F 7/02 | (2006.01) |
| A61F 7/00 | (2006.01) |
| A61L 15/26 | (2006.01) |
| A61L 15/18 | (2006.01) |
| A61L 15/30 | (2006.01) |

(52) U.S. Cl.
CPC .................. *A61D 9/00* (2013.01); *A61F 7/10* (2013.01); *A61L 15/18* (2013.01); *A61L 15/26* (2013.01); *A61L 15/30* (2013.01); *A61F 2007/0045* (2013.01); *A61F 2007/0228* (2013.01); *A61F 2007/0231* (2013.01); *A61F 2007/0249* (2013.01); *A61F 2007/0258* (2013.01); *A61F 2007/0277* (2013.01)

(58) Field of Classification Search
CPC ........... A61D 9/00; A01K 13/007; A61F 7/10; A61F 7/103; A61F 2007/105
See application file for complete search history.

(56) References Cited

U.S. PATENT DOCUMENTS

| 3,905,367 | A | 9/1975 | Dapcich |
| 5,152,285 | A | 10/1992 | Gnegy |
| 6,086,609 | A | 7/2000 | Buckley |
| 8,166,734 | B2 | 5/2012 | Ruetenik |
| 9,498,638 | B2 | 11/2016 | Ruetenik |
| 2002/0074136 | A1 | 6/2002 | Wiltz |
| 2010/0095641 | A1 | 4/2010 | Ruetenik |
| 2011/0271652 | A1* | 11/2011 | Wollowick ........... A01K 13/007 54/82 |

(Continued)

FOREIGN PATENT DOCUMENTS

WO 2015120368 A3 11/2015

*Primary Examiner* — Kaitlyn E Smith
(74) *Attorney, Agent, or Firm* — Trace H. Jackson; Rogers Towers, P.A.

(57) ABSTRACT

An equine thermal therapy overleg device that encircles a pastern of a subject horse and provides thermal therapy to the subject horse. The may include a pastern dual layer component, a distal phalanx cover and a distal phalanx slipper. The arrangement of the pastern dual layer component, a distal phalanx cover and a distal phalanx slipper allow for free movement of the subject horse and for a thermal fluid to contain ice and prevent the ice from becoming lodged around the subject horse hoof.

5 Claims, 8 Drawing Sheets

(56) References Cited

U.S. PATENT DOCUMENTS

| | | |
|---|---|---|
| 2012/0083725 A1 | 4/2012 | Mattes |
| 2012/0330376 A1 | 12/2012 | Flynn et al. |
| 2014/0209594 A1 | 7/2014 | Besner |
| 2015/0119772 A1 | 4/2015 | Ruetenik |
| 2015/0156989 A1 | 6/2015 | Ruetenik |
| 2015/0157435 A1 | 6/2015 | Chasins et al. |
| 2016/0100802 A1 | 4/2016 | Newman |
| 2016/0354232 A1 | 12/2016 | Rozental |
| 2017/0360541 A1* | 12/2017 | Orr ................. A01K 13/007 |

\* cited by examiner

EQUINE THERMAL THERAPY OVERLEG DEVICE

CROSS-REFERENCE TO RELATED APPLICATIONS

This application claims the benefit of U.S. patent application Ser. No. 15/626,081, filed on Jun. 17, 2017 entitled "Equine Cryotherapy Boot", which claims priority to U.S. Provisional Patent Application Ser. No. 62/351,955, filed on Jun. 18, 2016, entitled "Equine Cryotherapy Boot", the entire content of all are hereby incorporated by reference in its entirety.

FIELD OF THE DISCLOSURE

The present disclosure relates to apparatus and methods to effectively provide thermal therapy to a mid and lower leg region of an equine animal such as a horse, a mule, a donkey, a burro, a zebra, and so forth (generically, "horse"). More specifically, the present invention provides for an overleg device that allows a subject horse to move about and receive a requisite amount of thermal therapy.

BACKGROUND OF THE DISCLOSURE

Ice wraps around a horse leg have been known to provide relief of symptoms related to inflammation of the tissue experienced by the horse. However, known methods require that the horse be contained during therapy, which may last hours each day for many days. Previous designs of wraps to provide ice and/or water have not provided sufficient support for the therapy device and the horse often will dislodge the therapy device and disrupt the therapy if the horse is left to roam free.

Cryotherapy, or an ice therapy, may be effective to provide at least temporary relief of swelling. Swelling is a retention of fluid that may be due to one of a number of root causes, including physical injury (e.g., a sprain or a muscle strain) or as a byproduct of an infection or other disorder. One type of disorder is endotoxemia, which is associated with acute, high levels of endotoxins in the blood that can lead to septic shock. The formation of endotoxemia may be inhibited by matrix metalloproteinases (MMPs), also known as matrix-ins, which are calcium-dependent zinc-containing endopeptidases.

Currently, an efficient method to provide topical ice therapy continuously to a horse, that allows the animal to be mobile in a stall, does not exist. Most equine hospital staff provide topical ice therapy to a distal limb of a horse by placing the horse's foot in a five liter intravenous fluid bag, filling the intravenous bag with ice, and taping it to the horse's fetlock with duct tape. This methodology is cumbersome, time consuming and can create sores on the horse's skin.

Cold therapy boots have been developed, but the cold therapy boots only facilitate the placement of cold packs over the hoof capsule and do not provide cooling to the lower limb region of the horse. Several forms of large ice therapy boots and baths exist that effectively cool the foot and lower limb of the horse, but these products can only be used while the horse is stationary. Accordingly, a need exists for a device to facilitate cryotherapy for a horse, while allowing the horse to have mobility in a stall.

SUMMARY

Accordingly, the present invention provides a thermal containment device that may be generally described as an equine thermal therapy overleg device. The overleg device comfortably and safely provides topical thermal therapy to a horse's hoof and distal limb. Topical therapy typically will include chilled fluid, such as ice water, or ice salt water, but may also include warmed fluid. The equine thermal therapy overleg device also allows a horse receiving treatment to move freely without a need for being tethered. The design also facilitates easy and effective placement of a thermally beneficial substance, such as ice water or warm fluid or gel around a leg of a horse in the area below the horse's knee.

A thermal equine overleg device that includes a pastern dual layer component to encircle an area of an equine leg from a tarsus to a middle phalanx portion of a pastern of a horse being treated. A first fastening device secures the pastern dual layer component to the equine leg. In some embodiments, the first fastening device is fixedly attached along an outer longitudinal seam of the thermal equine overleg device for removably opening and closing the outer longitudinal seam.

The pastern dual layer portion includes an inner sleeve with a second fastening device, such as, for example a hook and loop securable tether for securing the inner sleeve around the equine leg from the tarsus to the middle phalanx of the horse being treated. The inner sleeve is fixedly attached to a shell layer and contains a thermal conveyer, such as, for example a thermal control fluid containing ice, in a containing area formed by securing of the inner sleeve around the portion of the equine leg from the tarsus to a middle phalanx portion of a pastern and additionally securing the shell layer around the equine leg and to a distal phalanx cover portion containing a distal phalanx slipper.

A fill port is used to introduce the thermal control fluid and/or ice into the containing area through at least the shell layer and in some embodiments through the inner sleeve.

In some embodiments, the first fastening device includes one or more hook and loop fasters placed along a rear surface of the pastern dual layer portion of the thermal equine overleg device secured to the equine leg being treated in a manner that allows for mobility of the horse being treated with thermal therapy using the thermal equine overleg device.

The thermal equine overleg device may further include distal phalanx cover to encircle a hoof of the equine leg wherein the distal phalanx cover encloses the hoof. Some embodiments may include the distal phalanx cover may be removably attached to the pastern dual layer portion. Embodiments may also include a distal phalanx cover that isolates a hoof of the equine leg from the thermal control fluid. The distal phalanx cover may be fashioned from a semi-porous material. In some embodiments, one or both of the distal phalanx cover and the pastern dual layer portion may include, at least an outer layer fashioned from a material containing one or more of: Kevlar®; poly-paraphenylene terephthalamide fiber; carbon fiber; fiberglass or other fiber reinforcement to provide increased durability and/or porous leachability for water to seep through.

The thermal equine overleg device of claim 1, further comprising a sensor to measure a thermal condition of one of the thermal control fluid and the equine leg.

In another aspect, an inner layer of the thermal equine overleg device may include a replaceable liner to provide for a sanitary application when the thermal equine overleg device is used multiple times.

Other aspects of the present invention include unique methods for treating a pastern of a subject horse with a thermal equine overleg device that allows for the horse being treated to move about in an untethered fashion during a treatment period. The method may include: securing a pastern dual layer portion of an equine thermal therapy boot around one or both of: a pastern and a canon of a horse being treated; securing an inner portion of the pastern dual layer portion of the equine thermal therapy boot to the area of the horse leg comprising from the tarsus to the middle phalanx of the horse leg via a fastening device such as a tether; securing a distal phalanx cover or an equine thermal therapy boot around a hoof corresponding with a portion of the horse leg to receive treatment; securing the distal phalanx cover to the pastern dual layer portion; and sealing a thermal control fluid in a fluid containment area between the inner portion of the equine thermal therapy boot and the area of the horse leg comprising from the tarsus to the middle phalanx of the horse leg via a tether.

In some additional method steps thermal control fluid may be replaced when a measured characteristic of the thermal control fluid changes, such as, for example, when the control fluid rises above a threshold beneficial temperature, or when a ratio of ice to liquid exceeds a threshold ratio. The thermal control fluid may be allowed to seep from the containment area at a predetermined rate, such as a rate enabled by a zipper used to secure the equine thermal therapy boot to the horse. Still other aspects include stimulating the horse leg with a secondary stimulation, such as, for example, a predetermined frequency of electromagnetic energy or acupuncture stimulation.

In some embodiments, an upper portion pastern dual layer component of the equine thermal therapy overleg device may have an inner portion that may attach to the horse leg from the carpus (knee) or tarsus (hock) to the fetlock (ankle) via elastic and hook-and-loop fastener straps as examples. The neoprene, or other water-holding or temperature-retentive material forming an outer portion of this part of the equine thermal therapy overleg device, may be sewn or secured to the inner portion of this part of the equine thermal therapy overleg device, and may be expandable on a lower area to hold ice and ice water. The bottom of this outer portion may attach to the lower portion distal phalanx cover of the equine thermal therapy overleg device with a zipper. A zipper or other fastener may also be used on the outer portion to facilitate frequent placement and replacement of ice or other thermal inducing material.

BRIEF DESCRIPTION OF THE DRAWINGS

The accompanying drawings, that are incorporated in and constitute a part of this specification, illustrate several embodiments of the disclosure and, together with the description, serve to explain the principles of the disclosure.

DETAILED DESCRIPTION

The present invention provides for methods and apparatus for application of thermal therapy to a pastern of a subject horse with a thermal equine overleg device. The TOED allows for the horse being treated to receive a cooling and/or warming therapy to a pastern during longer periods of time and while enjoying untethered movement during a treatment period. The present invention also includes methods of outfitting a horse with the equine thermal overlay device for treatment and removal of the equine thermal overlay device following a treatment period.

Figure 1:
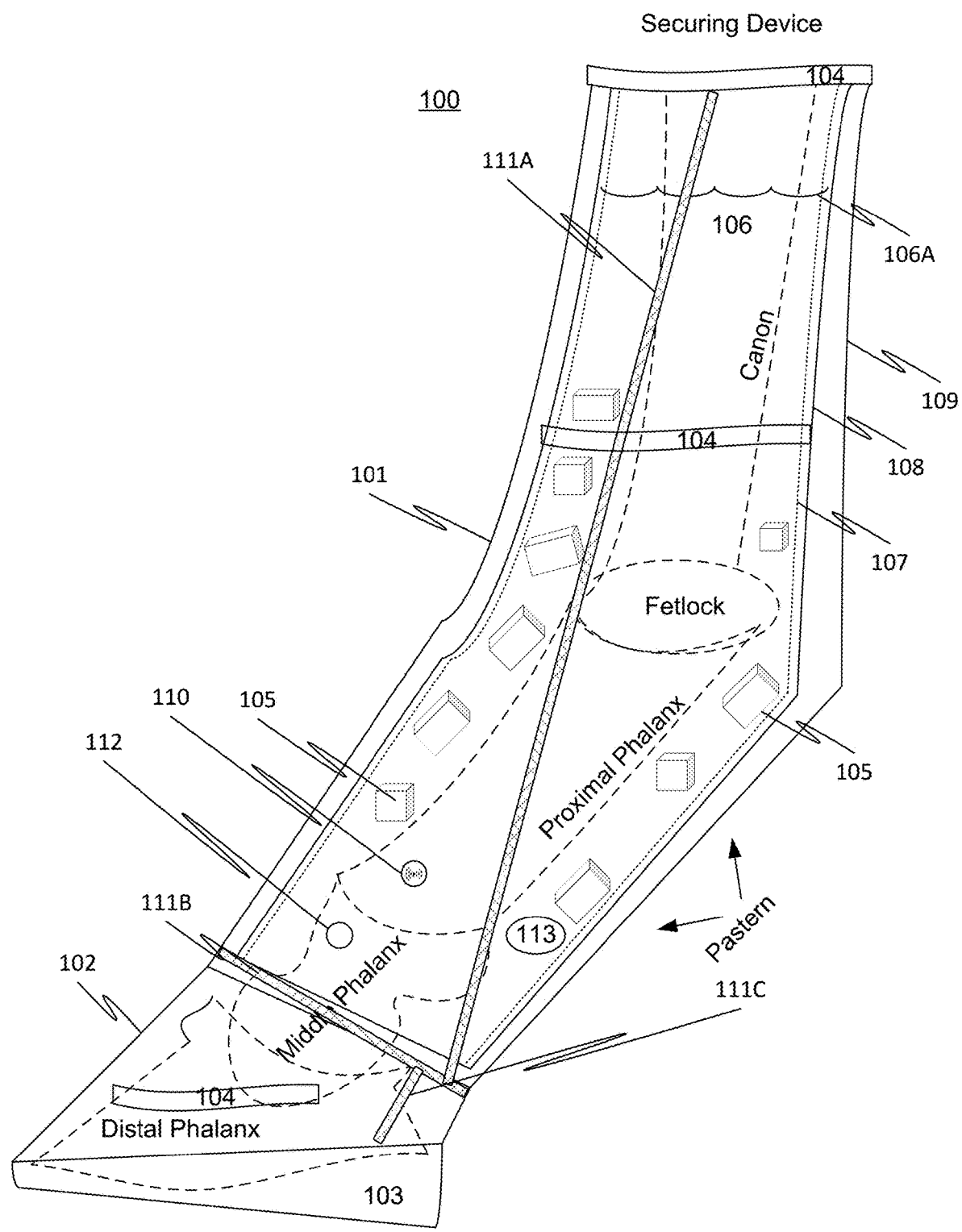
FIG. 1 illustrates an equine thermal therapy overleg device according to some embodiments of the present invention.

Referring now to FIG. 1, an equine thermal overlay device 100 according to the present invention generally covers an area of a horse leg that includes the pastern (proximal phalanx and middle phalanx and the hoof (distal phalanx) and may also continue up over the fetlock to cover all or some of the canon. The equine thermal overlay device 100 includes a pastern dual layer component 101 and a distal phalanx cover 102, a distal phalanx slipper 103 may be contained within the distal phalanx cover 102. In general, the pastern dual layer component 101 provides structural support to hold the distal phalanx cover 102 in place and allow a subject horse to move about while the 100 is in use. The distal phalanx cover 102 in turn secures the distal phalanx slipper 103 in place. The distal phalanx slipper 103 covers a lower area of a hood capsule and may proceed up along a partial area of a side of the distal phalanx but does not cover the distal phalanx.

In some preferable embodiments, the distal phalanx slipper 103 is formed from a durable yet compliant substance, such as, for example neoprene, neoprene, silicone and the like and must be capable of resisting deterioration form a horseshoe and support of the subject horse's weight. The distal phalanx slipper 103 provides a cushioning effect as a horse steps down on the distal phalanx slipper 103. The distal phalanx cover 102 is fashioned from a rugged material capable of resisting scuffs as a subject horse moves about and may strike the distal phalanx cover 102 against concrete and the like. The distal phalanx cover 102 is formed in shape to closely mimic a horse hoof (distal phalanx). Both the distal phalanx cover 102 and the distal phalanx slipper 103 may be formed in various matched sizes to accommodate different sized horse hooves. The distal phalanx cover 102 will include one or more reclosable fasteners, such as zippers 111B-111C for securing the distal phalanx cover 102 to the distal phalanx of the subject horse.

The distal phalanx cover 102 in turn secures the distal phalanx slipper 103 in place. The distal phalanx slipper 103 covers a lower area of a hood capsule and may proceed up along a partial area of a side of the distal phalanx, but does not cover the distal phalanx. The distal phalanx slipper 103 is replaceable independent of the distal phalanx cover 102 to accommodate wear in one or both of the distal phalanx cover 102 and the distal phalanx slipper 103. The distal phalanx slipper 103 is generally formed in a shape to mimic a shape of a hoof capsule. Some distal phalanx slipper 103 may be formed specific to a subject horse via custom manufacture. Additionally, the distal phalanx slipper 103 be formed with various shapes, such as a higher lift to accommodate a particular condition of a subject horse. By way of non-limiting example, a distal phalanx slipper 103 may be thicker to provide more lift, or thin to provide almost no lift, a slope from a front of the distal phalanx slipper 103 to a rear portion of the distal phalanx slipper 103 may also be varied to encourage or inhibit an amount of movement of a subject horse.

As discussed more fully below, in some preferred embodiments, the distal phalanx cover 102 is formed of material sufficiently flexible to turn the distal phalanx cover 102 inside out for placement on the distal phalanx, wherein the distal phalanx cover 102 may be "rolled" onto the distal phalanx with the distal phalanx slipper 103 positioned within the distal phalanx cover 102. The distal phalanx cover 102 contains the distal phalanx slipper 103 within the distal phalanx cover 102 and in place below the lower area of the distal phalanx. With the distal phalanx cover 102 rolled onto the distal phalanx and right side out, the one or more fasteners, such as zippers 111B-111C may be secured to hold the distal phalanx slipper 103 and the distal phalanx cover 102 over the distal phalanx.

Although the distal phalanx cover 102 is generally formed in the shape of a distal phalanx, the relatively short height of the distal phalanx cover 102 may not provide sufficient positioning support to move stay in proper position as the subject horse moves about. Therefore, the pastern dual layer component 101 is secured to the distal phalanx cover 102 with a fastening device, such as a zipper 111B. In some embodiments the pastern dual layer component 101 to distal phalanx cover 102 fastening zipper 111B is in a circumferential path around the distal phalanx cover 102. In addition, an adjustable strap device 104 may provide a variable amount of tension to one or both of the pastern dual layer component 101 and the distal phalanx cover 102 to facilitate a secure fit on the subject horse. In addition, portions of pastern dual layer component 101 and distal phalanx cover 102 may include a stretchable material to provide additional tensile positioning support.

The pastern dual layer component 101 is sized to be positionable around one or more of: a pastern, a fetlock and a canon of a subject horse. The pastern dual layer component 101 is secured in position via a zipper 111A or other device providing removeable attachment of the pastern dual layer component 101 to the subject horse. One or more fasteners, such as hook and loop straps may provide additional positioning tension to hold the pastern dual layer component 101 in a desired position relative to the leg of the subject horse.

The zipper 111A in a transverse position further permits a shape of the pastern dual layer component 101 to conform to a general shape of a subject horse leg. Whereas a simple pull over type leg wrap must accommodate a widest portion of the horse leg, the zipper 111A with a transverse placement allows the pastern dual layer component 101 to have sections narrower than a widest portion of a subject horse leg.

The pastern dual layer component 101 includes a first component that is an inner sleeve 108 fixedly attached via stitching, adhesive or the like to the outer cover 109. Optionally, a removeable liner 107 may be removeable attached to the inner sleeve 108. The inner liner 107 may be disposable with each use of the 100 and promote sanitary conditions for each subsequent use by protecting the inner liner 108 from exposure to any adverse conditions from a first application (such as infection) from being transferred via a second application of the 100.

The pastern dual layer component 101 may fastened to the subject horse with sufficient tension to secure the pastern dual layer component 101 and also hold the distal phalanx cover 102 in place and yet not adversely affect the subject horse by too much constriction. The fasteners 104 may be adjusted to provide a correct amount of tension.

In some embodiments, a thermal control fluid 106A is contained within a fluid containing area 106 proximate to a pastern of a subject horse. The thermal control fluid 106A may be chilled, and may contain ice 105. Alternatively, the thermal control fluid may be warmed to a predetermined temperature.

The thermal control fluid 106A may weep through a zipper 111A-111B or a dedicated weep passage 113. The weep passage may permit controlled passage of liquid from the fluid containment area 106 to an area external of the 100. In some preferable embodiments, ice 105 may melt in thermally controlled fluid 106A. The melted ice forms water that is by definition warmer than the ice. If too much water accumulates, the remaining ice will not be sufficient to adequately cool the thermal control fluid 106A. Therefore, weeping through the sipper, and/or a weep passage 113 maintains a correct ratio of ice and liquid in the thermal control fluid 106A to maintain a proper temperature range of the thermal control fluid 106A.

In some embodiments, one or both of the inner sleeve 108 and the outer cover 109 are impervious to water and thereby contain the thermal control fluid within the fluid containment area 106. By way of non-limiting example, the height of the pastern dual layer component 101 may vary from about 10 inches to about 20 inches.

Still further embodiments may include a sensor to provide feedback on a condition within the 100, and some embodiments may include a therapeutic stimulator, such as a specific wavelength of light or an acupressure or acupuncture administration device.

The thermally controlled fluid 106A may include chilled water, such as a mixture of ice and water, however, in some embodiments, a thermal cycling effect may be desired wherein the horse leg is first chilled and then warmed. In such embodiments, the thermally controlled fluid 106A may also include a warmed fluid. Temperature cycling is known to increase circulation, which may aid in healing and/or reducing inflammation. A zipper, or other seal may be included to close a fluid containing area 106 formed between an inner layer and an outer portion 108 that contains the thermally controlled fluid.

Figure 2:
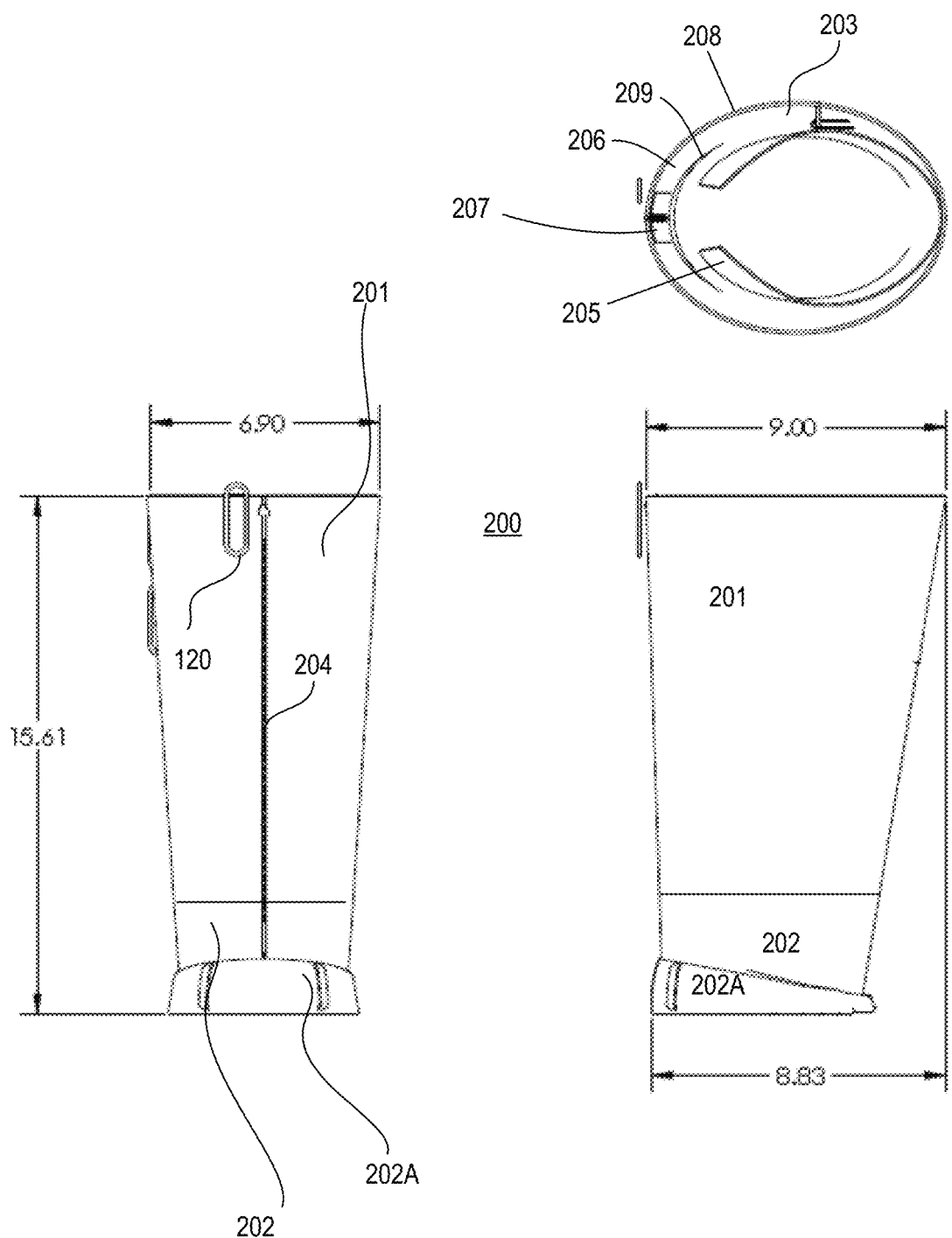
FIG. 2 illustrates an exemplary side view of an equine thermal therapy overleg device with chilled fluid contained within the boot.

Referring to FIG. 2, some exemplary embodiment of the present invention are illustrated to further describe some specific examples of an equine thermal therapy overleg device 200. The equine thermal therapy overleg device 200 comfortably and safely provides topical thermal therapy to a horse's hoof and distal limb. Topical therapy typically will include chilled fluid, such as ice water, or ice salt water, but may also include warmed fluid. The equine thermal therapy overleg device 200 also allows a horse receiving treatment to move freely in a stall or other area of limited movement. The design also facilitates easy and effective placement of a thermally beneficial substance, such as ice water or warm fluid or gel around the hoof and distal limb of the horse.

In general, the thermal containment device includes one or more pieces including a pliable, durable material that may be secured to a hoof wall. This could be done with various designs or materials, e.g., by a hook-and-loop fastener such as Velcro®, elastic straps, a grooved fastener and so forth. This portion of the equine thermal therapy overleg device 200 may have a zipper around a lower portion 202 to facilitate attachment of an upper portion 201 of the equine thermal therapy overleg device 200 to a horse leg. The lower portion 202 may range in a "hoof shaped" circumference of approximately 12 inches for a small boot, to approximately 20 inches for a large equine thermal therapy overleg device 200.

The upper portion 201 of the equine thermal therapy overleg device 200 may have an inner portion 209 including a tether 205 that will attach to the horse leg from the carpus (knee) or tarsus (hock) to the fetlock (ankle) via, for example, elastic or hook-and-loop fastener straps and so forth. The neoprene, or other water-holding or temperature-retentive material forming an outer portion 208 of the equine thermal therapy overleg device 200, may be sewn or otherwise fixedly attached to the inner portion 209 of the equine thermal therapy overleg device 200. A fluid-containing area formed between the inner portion 209 and the outer portion 208 of the equine thermal therapy overleg device 200 may be accessible to receive and contain a thermally controlled fluid or other substance. In some embodiments, the fluid containing area 206 may be expandable in a lower area to hold the thermally controlled fluid, such as ice and ice water. Additionally, some embodiments may include an additive to the thermally controlled fluid to keep the fluid generally microbe free and/or to provide better thermal stability.

A bottom of the outer portion 208 may be attachable to a lower portion 202 of the boot with a zipper, or other detachable securing device 202. A zipper may also be used on the upper portion 201 to facilitate frequent placement or repositioning of the ice or other thermally controlled substance. The height of the upper portion 201 may vary or be selectable, for example within a range of about 20-20 inches.

The bottom portion of the boot is preferably formed of a pliable, durable material and may be secured to the hoof wall. The bottom portion may be attached via, for example, hook-and-loop fastener and/or elastic straps. The bottom portion of the boot may also have a zipper around the lower portion 202 to facilitate attachment with the upper portion 201 of the boot. It may range in a "hoof shaped" circumference of approximately 12 inches for a small boot, to approximately 20 inches for a large boot.

The upper portion 201 of the boot may also include an inner portion 209, wherein the inner portion 209 is attachable to a horse leg from the carpus (knee) or tarsus (hock) to the fetlock (ankle) via securing devices 202 such as a tether 205. The securing devise may include, for example, one or both of: an elastic strap and a hook-and-loop fastener strap.

The upper portion 201 may also include a fluid containment area. The fluid containment pouch may be fashioned from an outer portion 208 material including neoprene or other fluid holding material. The outer portion 208 material of the upper portion 201 of the boot may be sewn or otherwise fixedly attached to an inner surface material. In preferred embodiments, the outer portion 208 material may be expandable to hold a thermally controlled fluid, such as ice and ice water.

A bottom of the upper boot may be removably attachable to the lower portion 202 of the boot with a zipper or other securing mechanism. A zipper or other securing mechanism also may be used to seal an opening between the inner liner and the outer liner and thereby facilitate timely placement of the ice or other thermal control substance. The height of the upper portion 201 is resizable between about ten inches to twenty (20 to 20) inches, according to an affected area and a size of the horse receiving treatment.

In some embodiments, the boot may be zipped and unzipped to rapidly treat a horse leg, e.g., by removing water that has been warmed by the environment or body heat, and refill the boot with ice and/or chilled water.

In some embodiments, the boot may be filled with one of various fluids, such as fresh water, salt water, an alcohol, glycol (i.e., antifreeze), an oil, or various mixtures or solutions thereof. The fluid may be selected based on a desirable characteristic, such as a lower melting point, a higher rate of heat transfer, heat retention, viscosity, animal safety in case of leaks, corrosiveness, inertness, stability, and so forth.

In some embodiments, an inner portion 209 of the equine thermal therapy over-leg device 200 may be wrapped tightly enough around a portion of the leg of interest (e.g., around the cannon portion) so that the equine thermal therapy overleg device 200 substantially does not move, slip, slide, etc. when filled with fluid. The equine thermal therapy overleg device 200 further may include an outer portion 208 that is impermeable to unintended leakage of fluid from within the equine thermal therapy overleg device 200 and infiltration of other fluids or other contaminants from outside the equine thermal therapy overleg device 200. In some embodiments, the equine thermal therapy overleg device 200 further may include a liner 207. The liner 207 may be provided as a layer situated between the inner portion 209 of the equine thermal therapy overleg device 200 and the leg of the animal. In other embodiments, the liner 207 may be provided as a layer or bladder that is internal to the equine thermal therapy overleg device 200. In some embodiments, the liner 207 may be a semi-porous material configured with microholes or the like, in order to allow fluid to leach or leak out intentionally at a slow rate, i.e., a rate at which may take several hours to drain the equine thermal therapy overleg device 200. A seeping equine thermal therapy overleg device 200 may be useful to help cool at least partially a larger area of a leg that what is covered directly by the equine thermal therapy overleg device 200 (e.g., by direct contact with the seepage, or by evaporation), and may be useful to make the equine thermal therapy overleg device 200 lighter and more comfortable over time for the animal when worn, or to provide greater mobility and range of motion while the equine thermal therapy overleg device 200 is worn.

In some embodiments, an outward-facing surface of the equine thermal therapy overleg device 200 may be insulated in order to reduce heat absorbed from the environment compared to heat absorbed from the animal.

In some embodiments, the equine thermal therapy overleg device 200 may include at least an outer portion 208 made from a puncture-resistant yet relatively lightweight material, such as Kevlar® coated neoprene. In some embodiments, the outer portion 208 may be selected from an alternate material providing a different desired quality, such as being water-retentive, flexible, stretchable, and so forth.

In some embodiments, a bottom of the equine thermal therapy overleg device 200 may completely enclose the hoof. In such embodiments, the bottom of the equine thermal therapy overleg device 200 (and side edges near the bottom) may be constructed to be more puncture-resistant than the top of the equine thermal therapy overleg device 200 in order to resist damage caused by the hoof as it bears the weight of the animal, or from sharp edges of the hoof, or from a horseshoe nailed to the hoof, and so forth. In at least some embodiments, it is not necessary for a portion of the equine thermal therapy overleg device 200 surrounding the hoof to provide cooling to the hoof.

In some embodiments, the equine thermal therapy overleg device 200 may be configured as a sleeve 203 that may surround but does not completely enclose the hoof, in particular the bottom of the hoof. Such embodiments do not need to be designed to withstand the weight of the horse, and may allow for easier draining of any seeping fluid. In some embodiments, the bottom of the sleeve 203 may extend no lower than the top of the hoof. In other embodiments, the bottom of the sleeve 203 may extend to the bottom of the sidewall 203 of the hoof, which may facilitate attachment of the lower portion 202 of the equine thermal therapy overleg device 200 to the leg because the hoof may provide a relatively solid surface to attach the equine thermal therapy overleg device 200.

In some embodiments, an equine thermal therapy overleg device 200 that encloses the hoof may be constructed in order to prevent or reduce ice from gathering under the hoof. For example, a predetermined amount of neoprene or the like may be used to form a water shoe with a non-slip surface underneath the hoof to shield the bottom of the hoof from ice. In some embodiments, a grating or the like may be used to allow ice to pass through the grate, while elevating the hoof above the ice.

In some embodiments, the equine thermal therapy overleg device 200 may include an integrated neoprene sack or the like to hold ice, in order to provide a more targeted or intense application of cryotherapy, or to apply the cryotherapy to a hard to reach location using the rest of the equine thermal therapy overleg device 200 alone. In some embodiments, a "soft" ice may be provided (i.e., having a temperature of about 32 degrees Fahrenheit (F)) or a water-ice mixture having a temperature of about 32 degrees F. to about 36 degrees F. In other embodiments, a "harder" ice may be provided (i.e., having a temperature less than 32 degrees F.). A harder ice may last longer before melting than a soft ice, but the harder ice may be too cold for the animal tissue, without additional insulation.

In some embodiments, dry ice may be used if additional insulation is provided in order to insulate the animal tissue from the temperature of dry ice (typically −209.3 degrees F.). The temperature felt by the animal tissue should be about 32 degrees F. to about 36 degrees F.

In some embodiments, cryotherapy may be applied to a relatively small localized area (e.g., to a smaller than normal hoof) by use of icepacks that are sized, contoured, or flexible to conform to the shape of a portion of the horse leg to be cooled. In some embodiments, a cloth portion may be provided to help guide a specific location for cryotherapy to be applied.

In some embodiments, the cryotherapy may be combined with a secondary therapy, e.g., an electromagnetic stimulation, an infrared therapy or a combination thereof. Embodiments may include a holder (e.g., a pocket, strap, hook and loop fastener, etc.) to secure to the equine thermal therapy overleg device 200 a source for the secondary stimulation therapy. Embodiments may include an opening or the like in the equine thermal therapy over-leg device 200 through which to apply the stimulation.

In some embodiments, the equine thermal therapy overleg device 200 may include status sensors 120. For example, status sensors 120 may include a fluid level indicator, a thermometer, a pressure sensor, an electronic sensor applied to the horse leg (e.g., to measure skin temperature, pulse rate, etc.), and so forth. The sensor data may be monitored and recorded over time. A processor coupled to a memory and to the sensor 120 may be provided, either as part of the boot, or remotely from the boot but communicatively coupled to the sensor (e.g., a wired or wireless interface). In some embodiments, the processor may be programmed by instruction code stored in the memory in order to provide a profile of treatment, either on demand or upon a regular schedule (e.g., a daily report). In some embodiments, the processor and communication interface may be configured to allow or provide remote access and/or control by a remote monitoring system or remote supervisory system. In some embodiments, the monitoring system or supervisory system may be configured to show a profile of treatment, e.g., as-provided treatment by itself, or as-provided treatment overlaid with sensor data, etc.

In some embodiments, a device to apply cryotherapy may be produced in configurations other than an equine thermal therapy overleg device 200. For example, a cryotherapy device may be fashioned in alternate configurations such as a water shoe, a bag, a knee brace, and so forth. An alternate configuration may be usable if a material it is made from includes a predetermined minimum insulation factor, and in addition may be at least partially porous and flexible (i.e., elasticity) A desired ratio of water to ice ratio may be controllable or selectable by selection of a material having a desired level of seepage. An excessive ratio of water to ice would be unnecessarily heavy and may cause sagging. In some embodiments, a ratio of ice and water of about 50% each works well. The ice/water ratio helps determine temperature of the cryotherapy device. Selecting a material with a high thermal impedance may tend to keep the cryotherapy device within a desired temperature range for a longer period of time.

A bottom plan view (upper right of FIG. 2), a rear plan view (lower left of FIG. 2) and a side right plan view (lower right of FIG. 2). The equine cryotherapy equine thermal therapy overleg device 200 includes a fastener 204 in a vertical dimension that may be used to secure the equine cryotherapy equine thermal therapy overleg device 200 to a horse. Typically, the fastener 204 may include a zipper and reside along a rear surface of the horse leg being treated. Other embodiments may include other fastener types such as hook and loop (e.g., Velcro), snaps, hook and eye or other removable fastener that fixedly secures the equine cryotherapy equine thermal therapy overleg device 200 in place on the horse leg.

The lower portion 202 may include a semi-formable material, such as a neoprene, rubber, latex, plastic, PVC or other material that may provide some cushion to the horse as the horse provides pressure on the lower portion 202. The lower portion 202 may be secured in place via a strap 205 or other securing device 202, as illustrated in the bottom plan view. The bottom plan view also includes sidewall 203.

Although some figures include specific dimensions, other embodiments may provide the cryotherapy equine thermal therapy overleg device in different dimensions, including different ratios of dimensions. For example, a larger equine thermal therapy overleg device 200 may be provided for larger breeds of mature horses (e.g., a Shire, a Percheron, a Clydesdale, or other draft horse, etc.), and a smaller equine thermal therapy overleg device 200 may be provided for smaller breeds of horses (e.g., an Arabian, a miniature breed, etc.), or for an immature horse of any breed (e.g., a pony).

Figure 3:
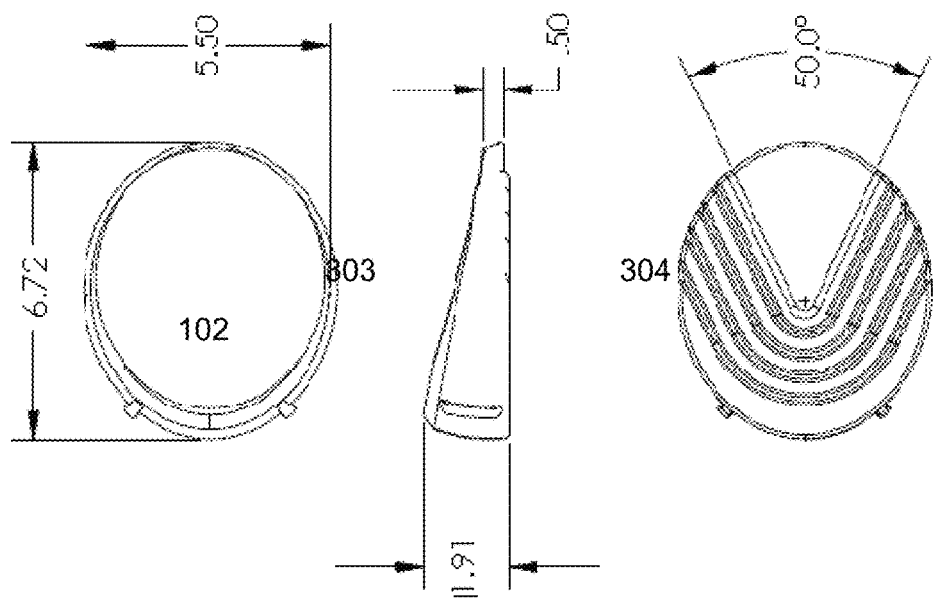
FIG. 3 illustrates various views of exemplary embodiments of a lower portion that may be fitted to a horse's hoof.
Figure 3:
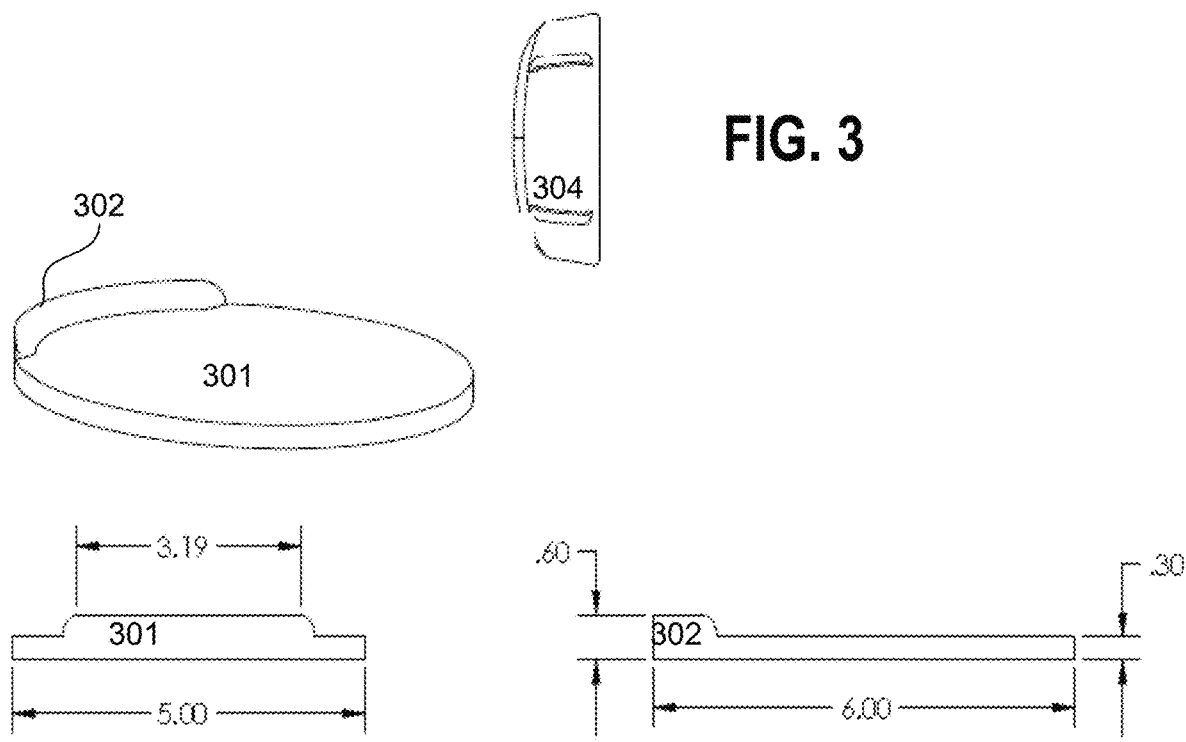

Referring now to FIG. 3, various views of exemplary embodiments of a lower portion distal phalanx cover 102 that may be fitted to a horse hoof are illustrated. A bottom portion 301 of the equine thermal therapy overleg device 100 may include a pliable, durable material that may be secured to the lower portion of the horse leg, such as a hoof wall 302. Securing to the horse may be done with various designs or materials; such as, for example, via hook-and-loop fastener and elastic straps. The lower portion distal phalanx cover 102 portion of the equine thermal therapy overleg device 100 may have a securing device 302, such as, by way of example, a zipper around the lower portion distal phalanx cover 102 to facilitate attachment to the upper portion pastern dual layer component 101 of the equine thermal therapy overleg device 100. Lower portion distal phalanx cover 102 may range in a "hoof shaped" circumference 303 of approximately 12 inches for a small equine thermal therapy overleg device 100, to 20 inches for a large equine thermal therapy overleg device 100.

An upper portion pastern dual layer component 101 of the equine thermal therapy overleg device 100 may be secured to the leg of the horse via an attachment mechanism that generally corresponds to a vertical dimension of the horse leg. By way of non-limiting example, the attachment mechanism may include a zipper fixedly attached to a seam in the upper portion pastern dual layer component 101. The seam may run along the length of the horse leg, or cover a vertical dimension of the horse leg in another pattern, such as a spiral pattern. The spiral pattern 304 may add strength to the overall fastening of the upper portion pastern dual layer component 101 of the equine thermal therapy overleg device 100 to the horse leg.

Figure 4:
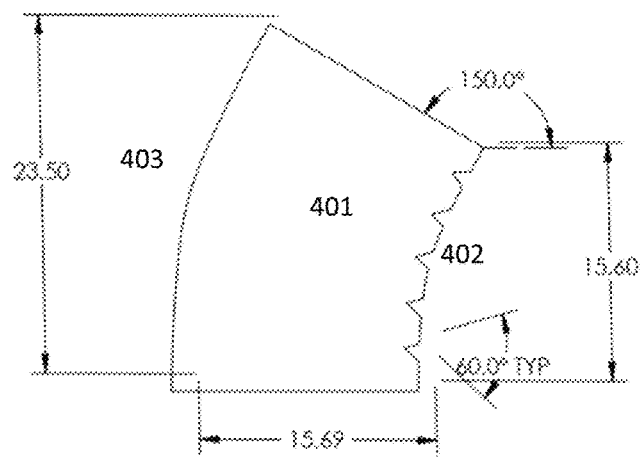
FIG. 4 illustrates an exemplary neoprene shell that may be used in some embodiments of the present invention.

Referring now to FIG. 4, an exemplary flexible shell 401, such as a neoprene shell that may be used in some embodiments of the present invention is shown. The shell may include a side compressed from flexing 402 and a side stretched from flexing 403.

Figure 5:
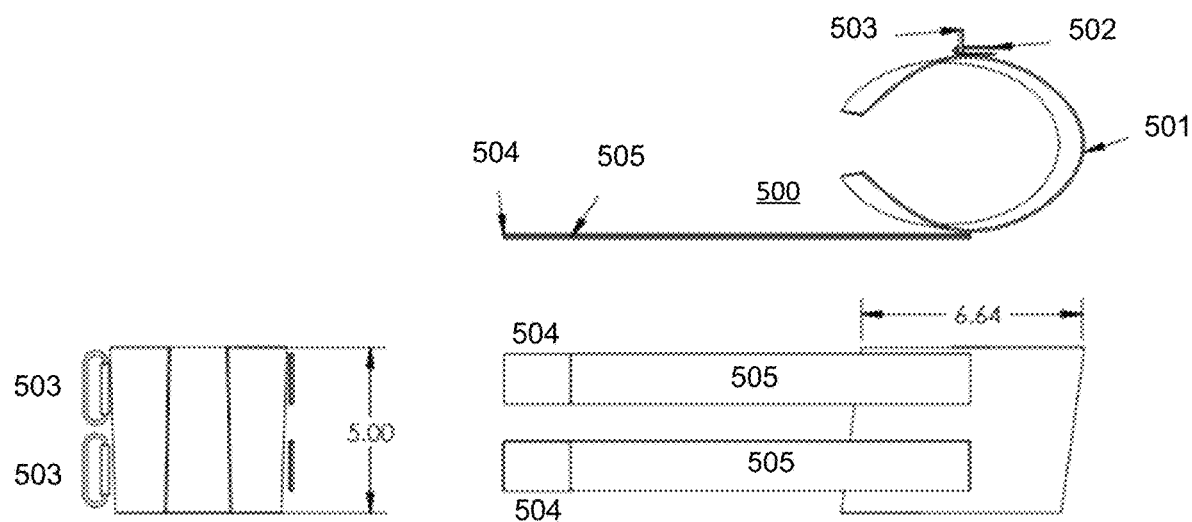
FIG. 5 illustrates an exemplary tether assembly that may be used in some embodiments of the present invention.

Referring now to FIG. 5, an exemplary tether assembly 500 is shown that may be used in some embodiments of the present invention. The tether assembly 500 may include an upper portion 501 with one or more straps 505. The straps 505 may interact with a buckle 503 and/or securing device 502. The straps 505 may also include a securing mechanism 504 on the end of the strap, such as hook and loop (e.g., Velcro), snaps, or hoop and eye.

Figure 6:
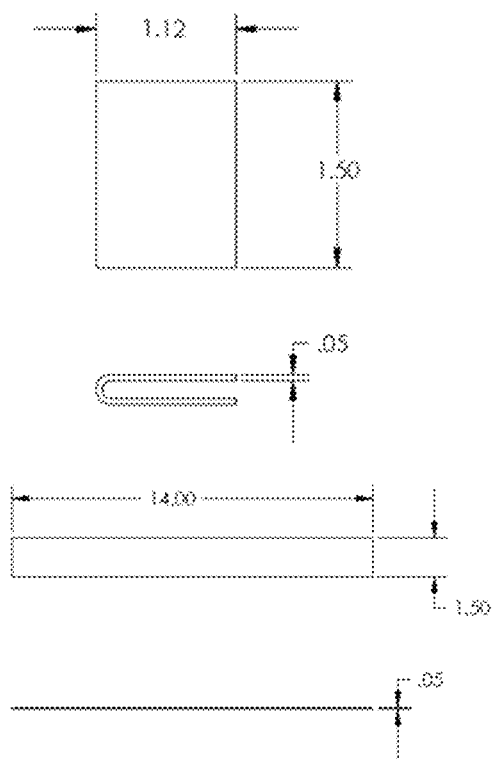
FIGS. 6-8 illustrate various exemplary views of securing devices that may be used in some embodiments of the present invention.
Figure 7:
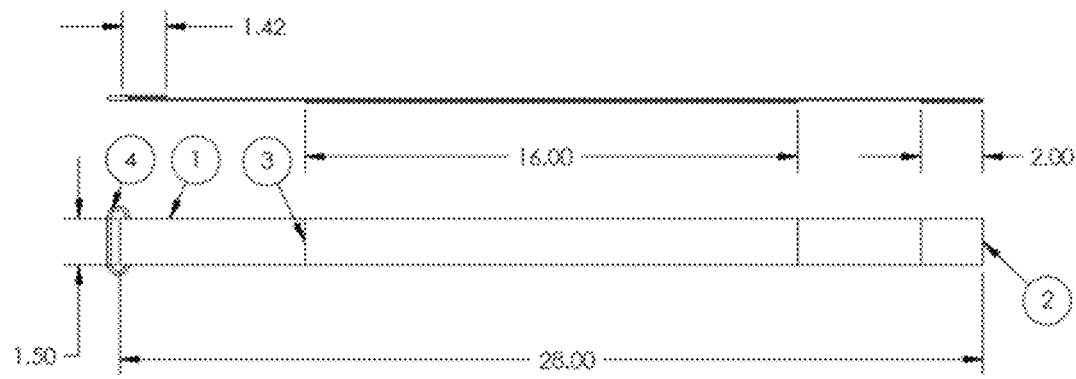
Figure 8:
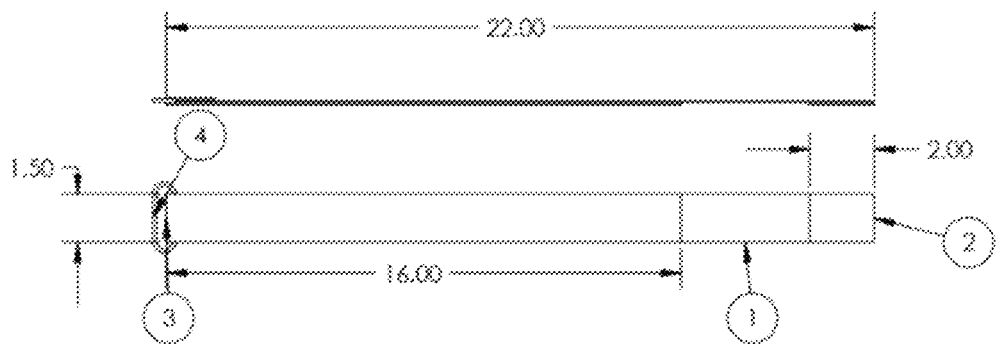

Referring now to FIGS. 6-8, various exemplary views of securing devices 202 that may be used in some embodiments of the present invention are illustrated.

Figure 9:
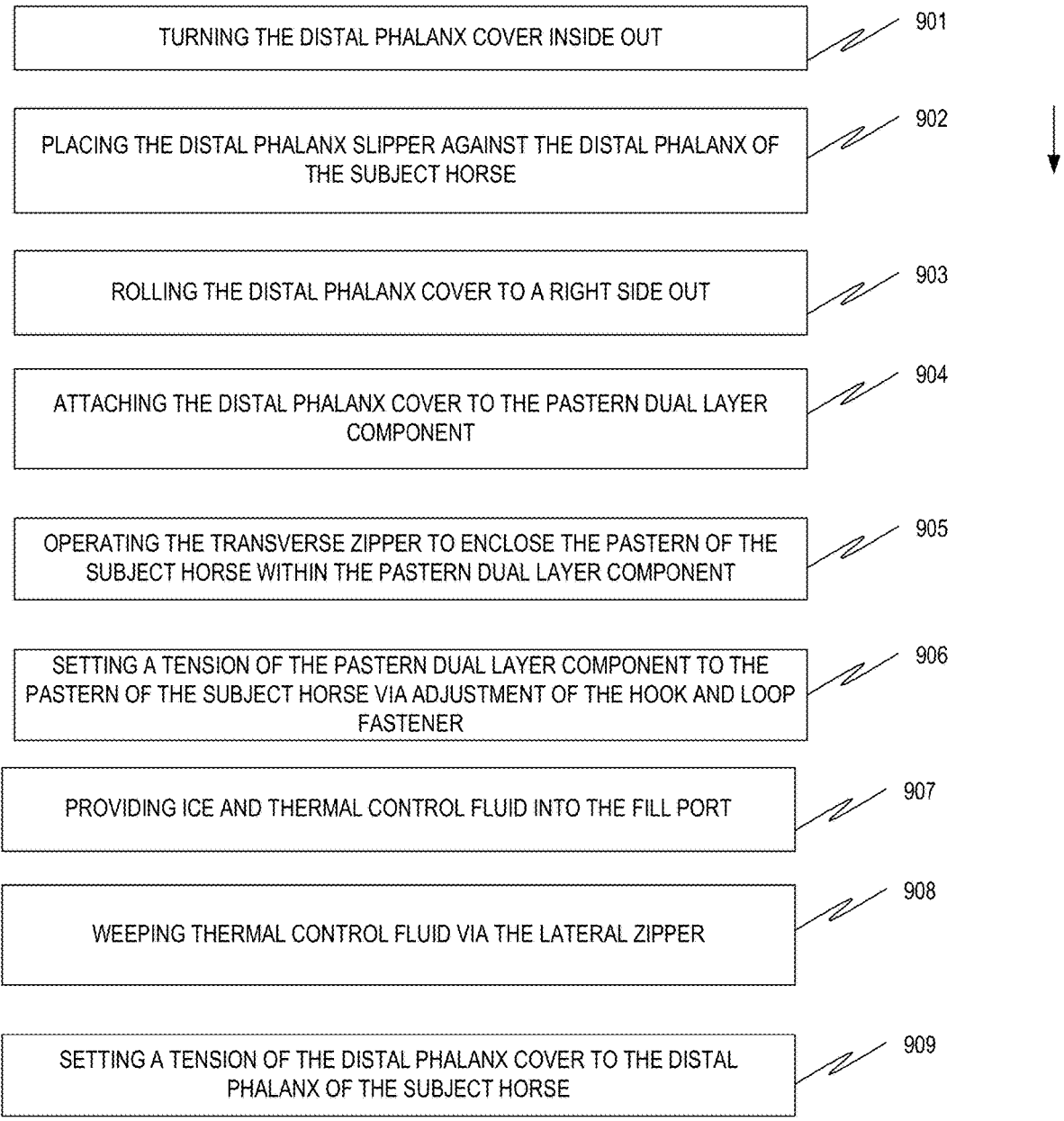
FIG. 9 illustrates exemplary method steps that may be conducted in some implementations of the present invention.

Referring now to FIG. 9, exemplary methods steps that may be executed in some implementations of the present invention are listed. At step 901 the distal phalanx cover is turned inside out; at step 902 the distal phalanx slipper is placed against the distal phalanx of the subject horse; at step 903 the distal phalanx cover is rolled to a right side out while covering the distal phalanx slipper and the distal phalanx of the subject horse with the distal phalanx cover; at step 904, at step 904, the distal phalanx cover is attached to the pastern dual layer component via operation of the lateral zipper; at step 905, the transverse zipper is operated to enclose the pastern of the subject horse within the pastern dual layer component; at step 906, a tension of the pastern dual layer component to the pastern of the subject horse is set via adjustment of the hook and loop fastener; at step 907, ice and thermal control fluid is provided into the fill port; and at step 908, thermal control fluid is weeped via the lateral zipper.

Figure 10:
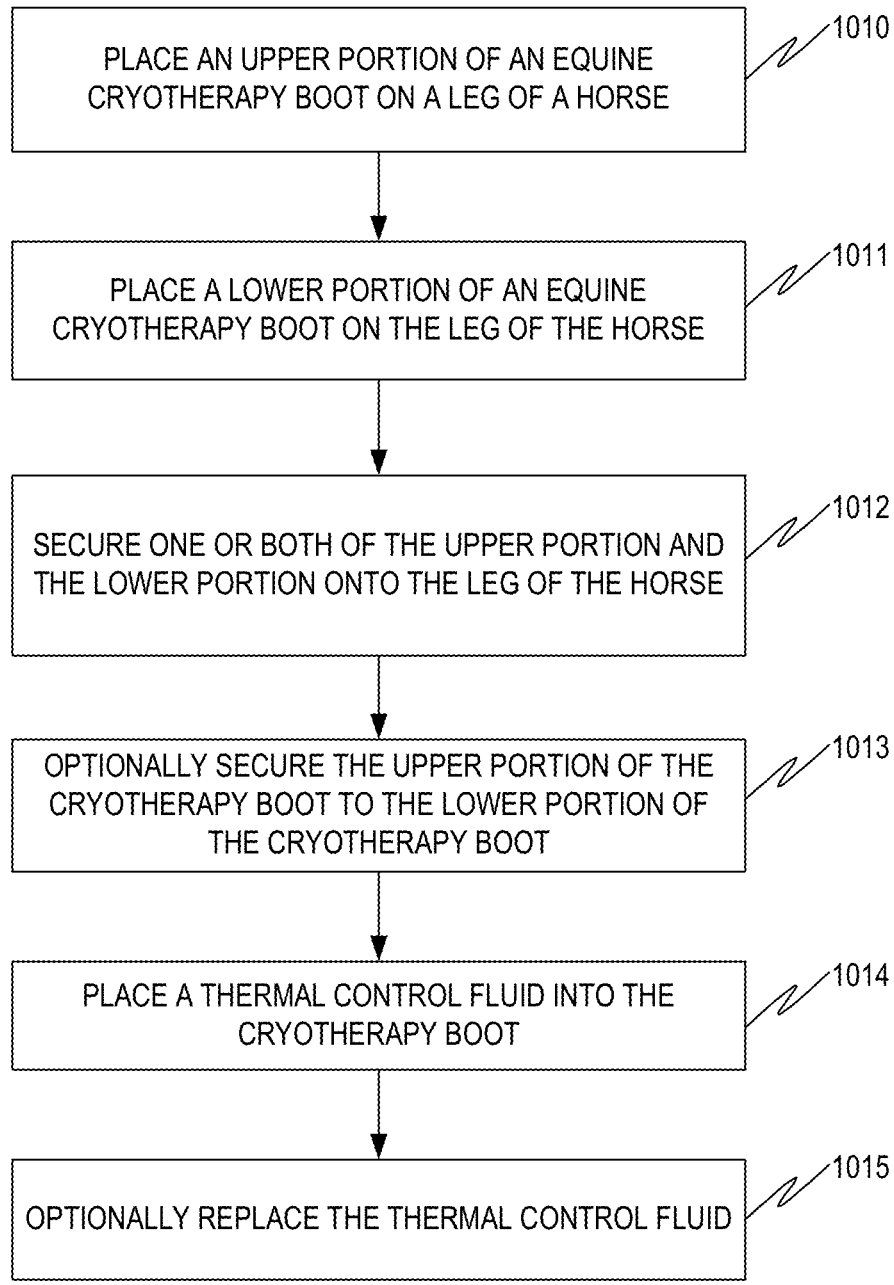
FIG. 10 illustrates exemplary method steps that may be conducted in some implementations of the present invention.

Referring now to FIG. 10, method steps that may be included in some embodiments of the present invention are listed. In an embodiment, the method may begin at step pastern dual layer component 1010, at which an upper portion pastern dual layer component 101 of an equine cryotherapy equine thermal therapy overleg device 100 is placed onto a leg of a horse.

Next, the method may progress to step pastern dual layer component 1011, at which a lower portion distal phalanx cover 102 of the equine cryotherapy equine thermal therapy overleg device 100 is placed onto a hoof of the horse.

Next, the method may progress to step pastern dual layer component 1012, at which one or both of the upper portion pastern dual layer component 101 and the lower portion distal phalanx cover 102 of the cryotherapy equine thermal therapy overleg device 100 may be secured onto the leg of the horse.

Next, the method may progress to optional step pastern dual layer component 1013, at which the upper portion pastern dual layer component 101 and the lower portion distal phalanx cover 102 of the cryotherapy equine thermal therapy overleg device 100 may be secured together.

Next, the method may progress to step pastern dual layer component 1014, at which a thermal control fluid may be placed into the cryotherapy equine thermal therapy overleg device 100. In other embodiments, the cryotherapy equine thermal therapy overleg device 100 may be pre-filled with thermal control fluid before the cryotherapy equine thermal therapy overleg device 100 is secured onto the horse leg.

Next, the method may progress to optional step pastern dual layer component 1015, at which the thermal control fluid may be replaced. For example, the fluid may be replaced if the fluid has warmed above a threshold temperature, or if more than a threshold amount of fluid has seeped from the cryotherapy equine thermal therapy overleg device 100.

CONCLUSION

A number of embodiments of the present disclosure have been described. While this specification contains many specific implementation details, there should not be construed as limitations on the scope of any disclosures or of what may be claimed, but rather as descriptions of features specific to particular embodiments of the present disclosure.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain embodiments, multitasking and parallel processing may be advantageous. Nevertheless, it will be understood that various modifications may be made without departing from the spirit and scope of the claimed disclosure.

What is claimed is:
1. An equine thermal therapy overleg device comprising:
a pastern dual layer component to encircle a section of an equine leg comprising a pastern and distal phalanx of a subject horse being treated, the pastern dual layer component comprising an outer cover and an inner sleeve;

the outer cover comprising a transverse zipper along an outer longitudinal seam for removably closing the outer longitudinal seam, said longitudinal seam enabling the pastern dual layer component to be fashioned into a shape mimicking the pastern of the subject horse;

a hook and loop fastener attached to the pastern dual layer component and positioned to allow adjustment of a tension between the pastern dual layer component and the pastern of the subject horse;

the inner sleeve fixedly attached to the outer cover, said inner sleeve comprising an inner sleeve fastener strap for adjusting tension between the liner to the pastern of the subject horse;

a fluid containing area to receive and contain a thermal control fluid and formed between the inner sleeve and the section of the pastern;

a fill port fixedly attached to the pastern dual layer component and positioned to introduce the thermal control fluid into the fluid containing area;

a distal phalanx cover sized encompass a distal phalanx of the subject horse and mimic a shape of the distal phalanx of the subject horse and wherein the distal phalanx cover isolates the distal phalanx of the subject horse from the thermal control fluid;

a lateral zipper removably attaching the distal phalanx cover to the dual layer component in a manner to provide sufficient attachment support via the lateral zipper to maintain the distal phalanx cover in position over the distal phalanx;

a distal phalanx slipper contained within the distal phalanx cover and positioned to receive the weight of the subject horse as the subject horse steps down, the distal phalanx slipper comprising a size and shape to receive a portion of the distal phalanx of the subject horse and the attachment of the distal phalanx cover to the dual layer component via the lateral zipper forming a seam around a circumference of the pastern that prevents ice from migrating down into the distal phalanx cover or between the distal phalanx slipper and the hoof of the subject horse;

a removable liner removably attached to the inner sleeve and providing a sanitary barrier between the inner sleeve and the subject horse; and wherein the pastern dual layer component comprises a portion of one or both of the distal phalanx cover and the outer cover comprising a semi-porous material positioned to allow thermal control fluid to weep through the semi-porous material.

2. The equine thermal therapy overleg device of claim 1, wherein the semi-porous material is configured to seep the thermal control fluid at a predetermined rate.

3. A method of attaching the equine thermal therapy overleg device of claim 1 to the subject horse, the method comprising the steps of:

turning the distal phalanx cover inside out;

placing the distal phalanx slipper against the distal phalanx of the subject horse;

rolling the distal phalanx cover to a right side out while covering the distal phalanx slipper and the distal phalanx of the subject horse with the distal phalanx cover;

attaching the distal phalanx cover to the pastern dual layer component via operation of the lateral zipper;

operating the transverse zipper to enclose the pastern of the subject horse within the pastern dual layer component;

setting a tension of the pastern dual layer component to the pastern of the subject horse via adjustment of the hook and loop fastener;

providing ice and thermal control fluid into the fill port;

weeping thermal control fluid via the lateral zipper.

4. The method of claim 3 further comprising the step of setting a tension of the distal phalanx cover to the distal phalanx of the subject horse.

5. The method of claim 3 further comprising the step of replacing the thermal control fluid when a measured characteristic of the thermal control fluid changes.

* * * * *